(12) United States Patent
Ferrone et al.

(10) Patent No.: US 7,592,421 B1
(45) Date of Patent: Sep. 22, 2009

(54) HLA CLASS II PEPTIDE MIMICS

(75) Inventors: Soldano Ferrone, Buffalo, NY (US); Wei Luo, Getzville, NY (US); Xinhui Wang, Williamsville, NY (US)

(73) Assignee: Health Research, Inc., Buffalo, NY (US)

( * ) Notice: Subject to any disclaimer, the term of this patent is extended or adjusted under 35 U.S.C. 154(b) by 601 days.

(21) Appl. No.: 10/804,392

(22) Filed: Mar. 19, 2004

Related U.S. Application Data

(60) Provisional application No. 60/455,833, filed on Mar. 19, 2003.

(51) Int. Cl.
 *C07K 7/00* (2006.01)
 *A61K 38/00* (2006.01)
(52) U.S. Cl. .................... 530/326; 530/327; 424/184.1; 424/185.1
(58) Field of Classification Search ........................ None
 See application file for complete search history.

(56) References Cited

OTHER PUBLICATIONS

Stevenson, FK et al. J. Imm. Meth. [1986] 86:187-190.*
Tutt, AL et al. J. Immunol. [1983] 131(6):3058-3063.*
Campbell, A. Monoclonal Antibody Technology [1985] pp. 1-32.*
Harlow, E. et al. Antibodies: A Laboratory Manual. [1988] pp. 72-77, 92-97, 128-135, 141-157, 271,274-275, 321-323 and 626-631.*
Chapman et al. *Immunization of Melanoma Patients with Antiidiotypic Monoclonal Antibody BEC2 (Which Mimics GD3 Ganglioside): Pilot Trials Using No Immunological Adjuvant*, Vaccine Research (1994) vol. 3, No. 2, pp. 59-69.
Grant et al. *Long Survival of Patients with Small Cell Lung Cancer After Adjuvant Treatment with the Anti-Idiotypic Antibody BEC2 Plus Bacillus Calmette-Guerin$^1$*, Clinical Cancer Research (Jun. 1999) vol. 5, pp. 1319-1323.
Lesinski et al. *A DNA Vaccine Encoding a Peptide Mimic of Streptococcus pneumoniae Serotype 4 Capsular Polysaccharide Induces Specific Anti-Carbohydrate Antibodies in Balb/c Mice*, Vaccine (2001) vol. 19, pp. 1717-1726.
Luo et al. *A Molecular Basis for Functional Peptide Mimicry of a Carbohydrate Antigen*, The Journal of Biological Chemistry (May 26, 2000) vol. 275, No. 21, pp. 16146-16154.
McCaffery et al. *Immunization of Melanoma Patients with BEC2 Anti-Idiotypic Monoclonal Antibody that Mimics GD3 Ganglioside: Enhanced Immunogenicity When Combined with Adjuvant*, Clinical Cancer Research (Apr. 1996) vol. 2, pp. 679-686.
Mittelman et al. *Human High Molecular Weight Melanoma-Associated Antigen (HMW-MAA) Mimicry by Mouse Anti-Idiotypic Monoclonal Antibody MK2-23: Induction of Humoral Anti-HMW-MAA Immunity and Prolongation of Survival in Patients with Stage IV Melanoma*, Proc. Natl. Acad. Sci. (Jan. 1992) vol. 89, pp. 466-470.

* cited by examiner

*Primary Examiner*—Ram R. Shukla
*Assistant Examiner*—F. Pierre VanderVegt
(74) *Attorney, Agent, or Firm*—Hodgson Russ LLP

(57) ABSTRACT

The present invention provides peptide mimics for HLA class II antigens. The peptide mimics were identified by panning phage display peptide libraries with anti-HLA class II monoclonal antibodies. The peptide mimics inhibit the binding of an anti-HLA class II antigen antibody to HLA class II antigen positive cells and also elicit antibodies which can bind to HLA class II antigen positive cells. The identified peptide mimics can be used as immunogens for therapy of diseases related to cells expressing the HLA class II antigen, such as Non-Hodgkins Lymphoma.

6 Claims, 4 Drawing Sheets

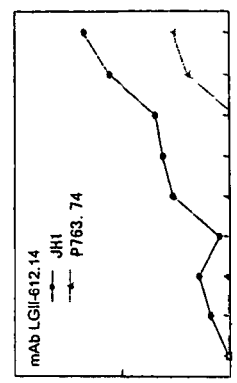
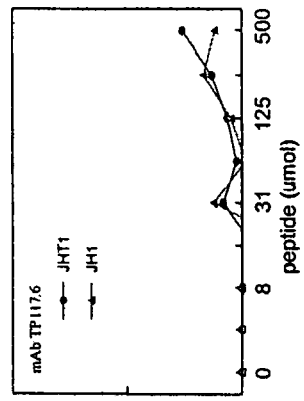
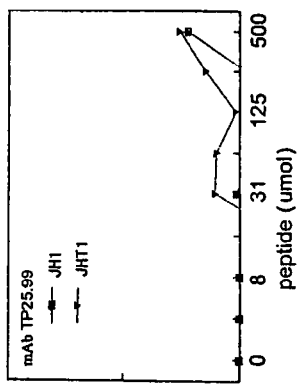
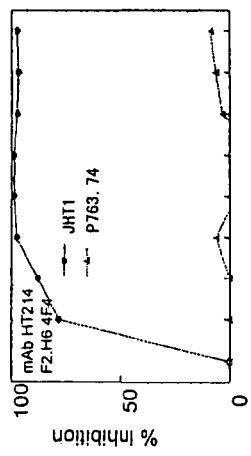
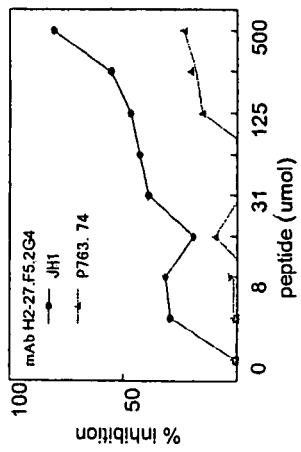
Figure 1A
Figure 1B
Figure 1C
Figure 1D
Figure 1E

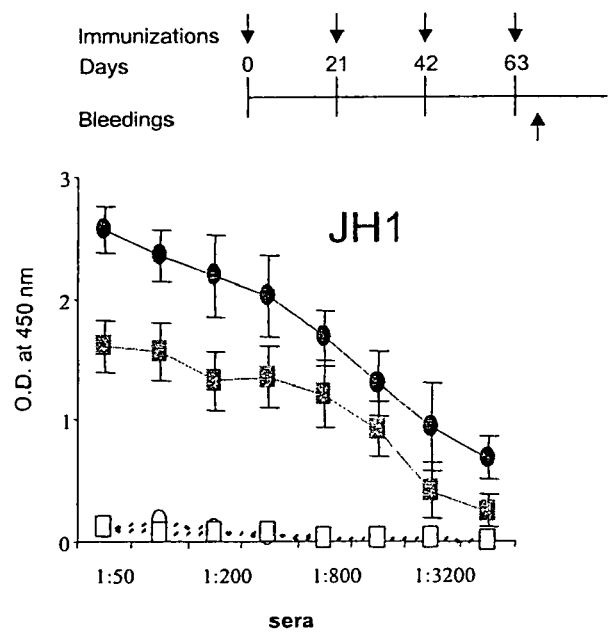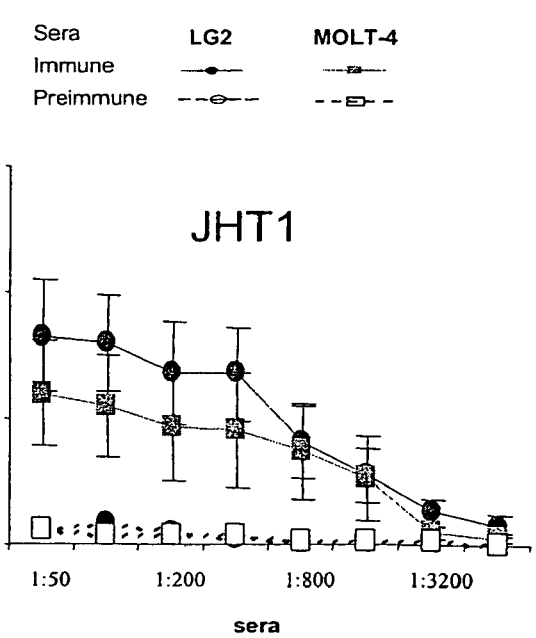
Figure 3A
Figure 3B

HLA CLASS II PEPTIDE MIMICS

This application claims priority to U.S. provisional application Ser. No. 60/455,833, filed Mar. 19, 2003 the disclosure of which is incorporated herein by reference.

This invention was supported by grant no. CA37959 from the National Institutes of Health. The Government has certain rights in the invention.

FIELD OF THE INVENTION

This invention relates generally to the field of the use of peptide mimics in the treatment of autoimmune diseases.

BACKGROUND OF THE INVENTION

In North America, Non-Hodgkin's lymphoma (NHL) is considered to be the fifth most common cancer [1]. Five-year relative survival rates for all stages of NHL in the United States from 1992-1997 was only about 53%. The diseases is correlated with human leukocyte antigen (HLA) class II self-antigen which is highly expressed in 95% of B-cell NHL. HLA class II usually exhibits a lack of immunogenicity which prevents initiation of immune responses in afflicted individuals and leads to disease progression. Accordingly, there is a need for a method of enhancing the ability of the immune system to recognize the HLA class II antigen.

Peptide mimics have been shown to elicit specific immune responses against self-antigens, including carbohydrate antigens such as Lewis antigens and *S. pneumoniae* serotype 4 capsular polysaccharide [2,3]. In several clinical trials, another kind of mimic to self-antigen, an anti-idiotypic antibody, has been shown to be able to elicit anti-self-antigen immune response [4-7]. However, there have been no peptide mimics developed to date that can elicit an immune response to the HLA class II antigen.

SUMMARY OF THE INVENTION

The present invention provides compositions in the form of peptide mimics of the HLA class II antigen and a method for producing same. This invention also provides a method of using the peptides to elicit an immune response against HLA class II antigen that is not normally immunogenic in hosts with HLA class II antigen expression.

Accordingly, in one aspect, the invention provides methods for identifying peptide mimics. The method comprises the steps of screening phage display peptide libraries with antibodies to HLA class II antigen. The identified peptides are then tested for their ability to elicit an immune response to HLA class II antigen and for reactivity of the elicited antibodies against HLA class II antigen bearing cells.

In another aspect, the present invention provides a method for eliciting an immune response in patients with NHL. The method comprises administering a composition effective in stimulating a specific immunological response against the HLA class II antigen. These composition(s) comprise a peptide that shares immunological characteristics of HLA class II antigen. While a detectable immunological response is likely to be beneficial, efficacy can also be deduced by an improvement in symptoms or control of the disease.

Still other embodiments include preparing a composition for use in the generation of an immune response and in the treatment of cells bearing HLA class II antigen. The composition comprises the peptide mimics disclosed herein.

BRIEF DESCRIPTION OF THE FIGURES

FIG. 1A is a graphical representation of data demonstrating that peptide JHT1 inhibits binding of mAb HT214.F2.H6.4F4 to HLA class II antigens to LG2 cells in a dose-dependent manner. Peptide 673.74 is a negative control peptide.

FIG. 1B is a graphical representation of data demonstrating that peptide JH1 inhibits binding of mAb H2-27.F5.2G4 to HLA class II antigen on LG2 cells in a dose-dependant manner. Peptide 673.74 is a negative control peptide.

FIG. 1C is a graphical representation of data demonstrating that peptide JH1 inhibits binding of mAb LGII-612.14 to HLA class II antigens on LG2 cells in a dose-dependent manner. Peptide 673.74 is a negative control peptide.

FIG. 1D is a graphical representation of data demonstrating that JH1 and JHT1 can inhibit binding of mAB TP117.6 to HLA class II antigens on LG2 cells.

FIG. 1E is a graphical representation of data demonstrating that peptides JH1 and JHT1 do not inhibit binding of mAb TP25.99, which recognizes HLA class I antigens, and is used as a control.

FIG. 3A is a graphical representation of results demonstrating that HLA class II peptide mimic JH1 can break self-tolerance and elicit a humoral immune response against HLA class II antigens in HLA-DR transgenic mice.

FIG. 3B is a graphical representation of results demonstrating that HLA class II peptide mimic JHT1 can break self-tolerance and elicit a humoral immune response against HLA class II antigens in HLA-DR transgenic mice.

DETAILED DESCRIPTION OF THE INVENTION

Figure 2A:
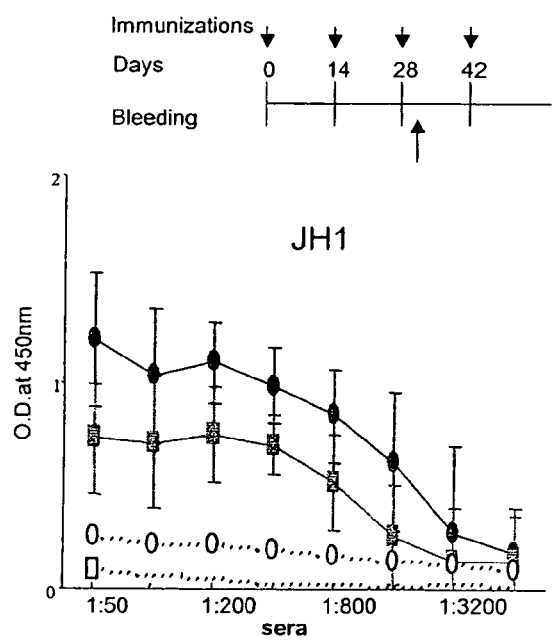
FIG. 2A is a graphical representation of data demonstrating that HLA class II peptide mimics JH1 elicits a humoral immune response against HLA class II antigens in BALB/c mice.

The present invention is generally directed to peptide mimics of HLA class II antigen which can be used in immunotherapy, particularly for NHL. The method comprises administering to an individual in need of treatment, a composition comprising peptide mimics of HLA class II antigen. While not intending to be bound by any particular theory, it is considered that the peptide mimics of HLA class II antigen as described herein will elicit an immune response against HLA class II antigen, which is usually not immunogenic in individuals with NHL, thereby providing a specific active immunotherapy for NHL and overcoming limitations associated with currently available NHL therapies, such as passive immunotherapy.

HLA class II peptide mimics have numerous advantages over existing NHL passive immunotherapies based on infusion of monoclonal or anti-idiotypic antibodies. For example, peptide mimics do not result in the typical side effects due to repeated antibody infusions into patients, peptide mimics are easier to modify and standardize than passive immunotherapies, and peptide mimics can elicit active (memory) immune responses which have much longer duration than passive monoclonal antibody therapies.

As will be described more fully by the Examples below, the HLA class II peptide mimics of the present invention were identified using phage display peptide libraries.

Specific peptides of the present invention can be isolated by a variety of methods based on their ability to bind to anti-HLA class II antibodies. For example, peptides characterized by specific anti-HLA class II antibody binding activity may be identified by screening a large collection, or library, of random linear peptides or cyclic peptides of interest. Cyclic peptide libraries include, for example, tagged chemical libraries comprising peptides and peptidomimetic molecules. Peptide libraries also comprise those generated by phage display technology. Phage display technology includes the expression of peptide molecules on the surface of phage as well as other methodologies by which a protein ligand is or can be associated with its encoding nucleic acid.

Screening phage-displayed random peptide libraries offers a rich source of molecular diversity and represents a powerful means of identifying peptide ligands that bind a receptor molecule of interest. For example, peptides are expressed on the tip of the filamentous phage M13, as a fusion protein with the phage surface protein pilus (at the N-terminus). Typically, a filamentous phage carries on its surface 3 to 5 copies of pili and therefore of the peptide. In such a system, few structural constraints are imposed on the N-terminus allowing the peptide to adopt many different conformations. However, biases in the distribution of peptides in the library may be caused by biological selection against certain of the peptides, which could reduce the diversity of peptides contained in the library.

Phage expressing binding peptides are selected by affinity purification with the target of interest. This system allows a large number of phage to be screened at one time. Since each infectious phage encodes the random sequence expressed on its surface, a particular phage, when recovered from an affinity matrix, can be amplified by another round of infection. Thus, selector molecules immobilized on a solid support can be used to select peptides that bind to them. This procedure reveals a number of peptides that bind to the selector and that often display a common consensus amino acid sequence. Biological amplification of selected library members and sequencing allows the determination of the primary structure of the peptide(s).

Peptide ligands identified by phage display screening frequently interact with natural binding site(s) on the target molecule, and often resemble the target's natural ligand(s). Many phage display peptide libraries are known to contain more than $10^9$ different peptides in each library (Scott, et al. 1990; Bonnycastle, et al. 1996). A peptide that binds to the antigen recognition site of the antibody is expected to have a 3D structure similar to the original antigen. By panning a phage display peptide library with anti-HLA class II mAb, HLA class II mimics, which specifically bind to the anti-HLA class II mAb can be isolated. Phage display peptide libraries have been shown to be useful in isolating peptide mimics of many different antigens, such as GD1á ganglioside (Ishikawa, et al. 1998), Lewis antigens (Luo, et al. 1998; Qiu, et al. 1999), MUC1 (Apostolopoulos, et al. 1999), E-selectin ligand (Fukuda, et al. 2000), anti-HER2/neu antibody (Park, et al. 2000), and capsular polysaccharide from *Streptococcus pneumoniae* (Lesinski, et al. 2001).

Methods for the production of phage display libraries, including vectors and methods of diversifying the population of peptides which are expressed, are well known in the art. (See, for example, Smith and Scott, Methods Enzymol. 217: 228-257 (1993); Scott and Smith, Science 249: 386-390 (1990); and Huse, WO 91/07141 and WO 91/07149). Cyclic peptide libraries also are well known in the art (see, for example, Koivunen et al., Methods Enzymol. 245: 346-369 (1994)). These or other well known methods can be used to produce a phage display library, from which peptides of the invention can be isolated using a variety of assays for binding to anti-HLA class II antibodies. Other methods for producing HLA class II antigen peptide mimics include, for example, rational design and mutagenesis.

Peptide mimics of HLA class II antigen can be isolated by panning phage display peptide libraries with anti-HLA class II antigen mAbs. Anti-HLA class II antigen mAbs can be used to isolate phage that display antibody reactive peptides. After phage panning, the binding ability of isolated phage colonies to anti-HLA class II antigen mAbs is tested with immunoscreening and further confirmed by enzyme-linked immunosorbent assay (ELISA). Anti-HLA class II antigen antibody reactive phage clone and the same phage without displaying peptides, can be utilized as a positive and a negative controls respectively in the immunoscreening and ELISA. In the positive phage clones, the DNA inserts that encode the antibody reactive peptides can be sequenced. Peptides can be synthesized based on the sequences of the DNA inserts. The synthesized peptides are tested in ELISA to determine their binding reactivity with corresponding anti-HLA class II antigen mAbs. The ability of synthetic peptides to inhibit the binding of anti-HLA class II antigen mAbs to HLA class II antigen can be tested in an inhibition assay with HLA class II antigen-positive cell lines. The synthetic peptides that inhibit or block the binding of anti-HLA class II antigen mAbs to HLA class II antigen can be tested as active immunotherapy candidates.

Panning phage display peptide libraries with anti-HLA class II antigen mAbs can be performed by routine procedures. For example, panning can be performed in 96-well microtiter plates (Falcon, Becton Dickinson, Lincoln Park, N.J.) as described previously (Bonnycastle, et al. 1996). A suitable amount of anti-HLA class II antigen mAbs (0.5-5 μg/well) can be immobilized on an anti-mouse IgG (1+2a+2b+3) Fc' fragment coated 96-well microtiter plate. Phage display peptide libraries (1012 virions/well) can be added to the anti-HLA class II antigen mAb coated plates and incubated for a suitable period of time to effect specific binding (4° C. for 4 hours). After the incubation, the bound phage can be eluted. The eluted phage is incubated in wells coated with anti-mouse IgG (1+2a+2b+3) Fc' fragment antibody at 4° C. for an additional 1-2 hours to eliminate phage that bind to the anti-mouse IgG antibody. Phage in the supernatant can be amplified (in *E. coli* K91kan prepared as described by Smith, et al. 1993) and used for subsequent rounds of panning. Phage enrichment after each round of panning can be determined by spot titering on NZY plates containing tetracycline (20 μg/ml), as described by Smith and Scott (Smith, et al. 1993).

The binding ability of phage clones isolated following subsequent rounds of panning with anti-HLA class II antigen mAbs can be examined by immunoscreening. The binding activity of positive phage clones to anti-HLA class II antigen mAbs can also be confirmed by ELISA. The procedures of immunoscreening are known to those skilled in the art (see Christian, et al. 1992). Briefly, phage clones on NZY plates can be transferred onto nitrocellulose membranes. The nitrocellulose membranes are incubated with labeled (biotinylated) anti-HLA class II antigen mAbs in a suitable buffer (TNT7.5 buffer and 20% FCS for 2 hours). The membranes are washed and then incubated with a detecting agent (such as horseradish peroxidase (HRP)-conjugated streptavidin for 30 minutes). After incubation, antibody bound phage clones can be detected by standard methods. Positive phage clones identified by immunoscreening can be cultured in multi-well plates. The phage supernatants can be collected and subjected to ELISA.

For sequencing of the DNA inserts from phage clones reacting with anti-HLA class II mAbs, double stranded DNA is extracted by using commercially available kits (QIA prep. Spin, Miniprep kit, Qiagen Inc., Valencia, Calif.) from phage infected *E. coli* culture. The DNA sequencing can be performed with suitable primers and DNA sequencing carried out by standard techniques.

Peptides identified according to this invention can be tested for their ability to bind to anti-HLA class II antibodies and to elicit anti-HLA class II antibodies. The peptides of the present invention can be synthesized using methods well known in the art. Such methods include recombinant DNA methods and chemical synthesis. Recombinant methods of producing a peptide through expression of a nucleic acid sequence encoding a peptide in a suitable host cell are well known in the art, such as is described in Sambrook et al., Molecular Cloning: A Laboratory Manual, 2nd Ed, Vols 1 to 3, Cold Spring Harbor, N.Y. (1989), which is incorporated herein by reference.

Peptides of the invention can also be produced by chemical synthesis, for example, by the solid phase peptide synthesis of Merrifield (Merrifield et al., J. Am. Chem. Soc., 85:2149 (1964), incorporated herein by reference). Standard solution methods well known in the art also can be used to synthesize a peptide of the present invention (see, for example, Bodanszky, M., Principles of Peptide Synthesis (Springer-Verlag, 1984), which is incorporated herein by reference). Newly synthesized peptides can be purified, for example, by high performance liquid chromatography (HPLC), and can be characterized using, for example, mass spectrometry or amino acid sequence analysis.

A newly synthesized linear peptide can be cyclized by the formation of a bond between reactive amino acid side chains. For example, a peptide containing a cysteine-pair, or any of the cysteine analogs can be synthesized, and a disulfide bridge can be formed by oxidizing the peptide with 0.01 M $K_3Fe(CN)_6$ at pH 8.4. Alternatively, a lactam, a lysinonorleucine or a dityrosine bond can be formed. Methods for forming these and other bonds are well known in the art and are based on well established principles of chemical reactivity (Morrison and Boyd, Organic Chemistry, 6th Ed. (Prentice Hall, 1992).

A peptide of the present invention also can be cyclized by forming a peptide bond between non-adjacent amino acid residues as described, for example, by Schiller et al., Int. J. Pept. Prot. Res. 25:171 (1985), which is incorporated herein by reference. Peptides can be synthesized on the Merrifield resin by assembling the linear peptide chain using Nα-Fmoc-amino acids and Boc and tertiary-butyl proteins. Following release of the peptide from the resin, a peptide bond can be formed between the amino and carboxyl termini.

The peptide mimics of the present invention can be used for therapeutic purposes. More specifically, the therapeutic method generally referred to herein could include methods for the treatment of pathologies associated with HLA class II antigen expressing cells by the administration of pharmaceutical compositions that comprise the mimic peptide(s), variants, analogs or active fragments thereof, effective inhibitors or enhancers of activation of the mimic peptide(s), or other equally effective drugs developed for instance by a drug screening assay prepared and used in accordance with a further aspect of the present invention. For example, the mimic peptide(s) of the present invention, variants, analogs or active fragments thereof, as particularly represented by any of SEQ ID NOS: 1-8 may be administered to generate a humoral immune response in individuals with NHL.

The peptide mimics can be used as agents for inducing an immune response in an individual. Accordingly, it is an object of the present invention to provide peptides that mimic the HLA class II antigen. In another embodiment, the invention comprises a method of administering HLA class II peptide mimics to an individual with NHL such that a humoral immunological response to the HLA class II antigen in the individual is elicited.

Immunogenic compositions typically contain pharmaceutically acceptable vehicles, such as water, saline, glycerol, ethanol, etc. Additionally, auxiliary substances, such as wetting or emulsifying agents, pH buffering substances, preservatives, and the like, may be included in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect. The proteins may also be incorporated into Immune Stimulating Complexes together with saponins, for example Quil A (ISCOMS).

Immunogenic compositions used to raise antibodies comprise a 'sufficient amount' or 'an immunologically effective amount' of the peptides of the present invention, as well as any other of the above mentioned components, as needed. 'Immunologically effective amount', means that the administration of that amount to an individual, either in a single dose or as part of a series, is effective to provoke an immune response and to raise antibodies, as defined above. This amount varies depending upon the health and physical condition of the individual, the taxonomic group of the individual to be treated (e.g. nonhuman primate, primate, rabbit, etc.), the capacity of the individual's immune system to synthesise antibodies, the immunogenicity of the antigenic peptide, and its mode of administration, and other relevant factors. It is expected that the amount will fall in a relatively broad range that can be determined through routine trials. Usually, the amount will vary from 0.01 to 1000 mg/dose, more particularly from 0.1 to 100 mg/dose. Subsequent to initial administration, individuals may be boosted by readministration. In some preferred embodiments, multiple administrations are performed.

The immunogenic compositions are conventionally administered parenterally, typically by injection, for example, subcutaneously or intramuscularly. Additional formulations suitable for other methods of administration include oral formulations and suppositories. Dosage treatment may be a single dose schedule or a multiple dose schedule. The immunogenic compositions may be administered in conjunction with other immunoregulatory agents.

For parenteral administration, the compound can be formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques.

Suitable pharmaceutical carriers are described in Remington's Pharmaceutical Sciences (18th Edition, A. R. Gennaro et al. Eds., Mack Publishing Co., Easton, Pa., 1990), a standard reference text in this field. A pharmaceutically acceptable formulation will provide the active ingredient(s) in proper physical form together with such excipients, diluents, stabilizers, preservatives and other ingredients as are appropriate to the nature and composition of the dosage form and the properties of the drug ingredient(s) in the formulation environment and drug delivery system.

So that the invention described herein may be more fully understood, the following detailed Examples are set forth. The Examples are in no way meant to limit the breadth of the claims, but rather to specifically point out novel aspects of the present invention.

EXAMPLE 1

This Examples illustrates the identification of the peptide mimics of the present invention. HLA class II peptide mimics, JHT1, JH1 and JH2 (Table 1), were isolated by panning phage display peptide libraries, pVIII LX-8 and pVIII $X_{15}$, with anti-HLA class II monoclonal antibodies (mAb) H2-27.F5.2G4, HT214.F2.H6.4F4, LGII612.14 and TP117.6.

Phage display peptide libraries X15 and LX-8 (XCX8CX) displaying 15 amino acid random, linear peptides and 8 amino acid random, linear peptides, respectively, were kindly provided by Dr. J. K. Scott (Simon Fraser University, Burnaby, British Columbia, Canada). The peptide libraries were constructed using bacteriophage vector f88.4 and had random peptide inserts at the N terminus of the synthetic pVIII major coat protein. Peptides were synthesized utilizing an ABI peptide synthesizer in Molecular Genetics Instrumentation Facility, University of Georgia, Athens, Ga.

TABLE 1

| Panning with mAb | Peptide sequence | |
|---|---|---|
| H2-27.F5.2G4 | SCLRAGGWVCCK(JH1) | (SEQ ID NO:1) |
| | YCGYTNEYKCCY(JH2) | (SEQ ID NO:2) |
| | MTTRVTRTAGNNAVS(JH3) | (SEQ ID NO:3) |
| | QPSLTGIQRPEFQLR(JH4) | (SEQ ID NO:4) |
| HT214.F2.H6.4F4 | KCPLDPKGLNCV(JHT1) | (SEQ ID NO:5) |
| LGII-612.14 | SCLRAGGWVCCK(JH1) | (SEQ ID NO:6) |
| | YCGYTNEYKCCV(JH2) | (SEQ ID NO:7) |
| TP117.6 | LRASIFGEIPTRTSS(JTP1) | (SEQ ID NO:8) |

For isolating HLA class II peptide mimics, biotinylated anti-HLA class II mAbs H2-27.F5.2G4, HT214.F2.H6.4F4, LGII612.14 and TP117.6 were immobilized on a 96 well plate which was pre-coated with streptavidin by 0.1M $NaHCO_3$ at pH 9.6. The antibody-coated plate was blocked by a blotto solution at room temperature for 2 hours. 50 ul of blotto and 100 ul of $10^{12}$ virions from pVIII LX-8 and pVIII $X_{15}$ libraries were added to the blocked plate and incubate in a humidified box at 4° C. for 4 hours. After washing with TBS six times, the bound phage were eluted by 35 ul elution buffer (0.1 M Hydrochloric acid, pH 2.2) at room temperature for 10 minutes followed by pH neutralization with an alkaline solution (1 M Tris, pH 9.1). The phage-containing eluted solution was used to transform 5 ul of $5 \times 10^9$ mid log phase starved K91kan (*E. coli*) cells followed by incubation at room temperature for 15 minutes. The mixture was added 133 ul 0.2 ug/ml tetracycline super broth and incubated in a humidified box at 37° C. for 40 minutes with shaking at 150 rpm. To the mixture was added 20 ul of 150 ug/ml tetracycline super broth followed by incubation in a humidified box at 37° C. with shaking at 150 rpm for an additional 20 hours.

The mixture was then centrifuged at 400 rpm for 30 minutes and the supernant of the mixture was stored at 4° C. for next round of panning. The panning procedure was repeated three times to enrich the specific binding phage. After the third biopanning, phage-infected K91kan culture supernatants were plated (in 10× dilutions) onto NZY agar plates containing 100 ug/ml tetracycline. Presence of positive phage clones on these plates was examined by immunoscreening and reverse ELISA procedures known to those skilled in the art with anti-HLA class II mAbs H2-27.F5.2G4, HT214.F2.H6.4F4, LGII612.14 and TP117.6. The DNA sequences expressing the anti-HLA class II mAb binding peptide on phage were then sequenced, the corresponding amino acid sequences deduced and the peptides synthesized.

EXAMPLE 2

This Example illustrates the ability of the peptide mimics to bind to anti-HLA class II mAbs. The synthetic peptides were tested by ELISA for their ability to bind to anti-HLA class II mAb H2-27.F5.2G4, HT214.F2.H6.4F4, LGII612.14 and TP117.6. JH1 and JHT1 were also tested for their ability to inhibit the binding of anti-HLA class II mAb H2-27.F5.2G4 (FIG. 1B), HT214.F2.H6.4F4 (FIG. 1A), LGII612.14 (FIG. 1C) and TP117.6 (FIG. 1D) to HLA class II bearing cells LGL2 cells. H2-27.F5.2G4, LGII-612.14 and HT214.F2.H6.4F4 are monoclonal antibodies (mAb) that recognize HLA class II antigens. TP25.99 is a monoclonal antibody (mAb) which recognizes HLA class I antigens and is used in FIG. 1E as a control. LG2 is a human lymphoid cell line which expresses HLA class II antigens on its cell surface. P763.74 is a High Molecular Weight-Melanoma Associated Antigen (HMW-MAA) peptide mimic isolated using the anti-HMW-MAA mAb 763.74 and is used in FIGS. 1A-1C as a control peptide. The peptides were considered to be mimics of HLA class II antigens if they could inhibit the binding of any of the four anti-HLA class II mAb (H2-27, F5.2G4, HT214.F2.H6.4F4, LGII612.14 and TP117.6) to HLA class II bearing cells. Among them, the peptides JH1 (SEQ ID NO:1) and JHT1 (SEQ ID NO:5) reacted with the combining sites of the mAb H2-27.F5.2G4 and LGII-612.14, and HT214.F2.H6.4F4, respectively, as indicated by their ability to bind to anti-HLA class II mAb and to inhibit the binding of anti-HLA class II mAb to HLA class II bearing cells (FIGS. 1A-1C and FIG. 1E).

EXAMPLE 3

Figure 2B:
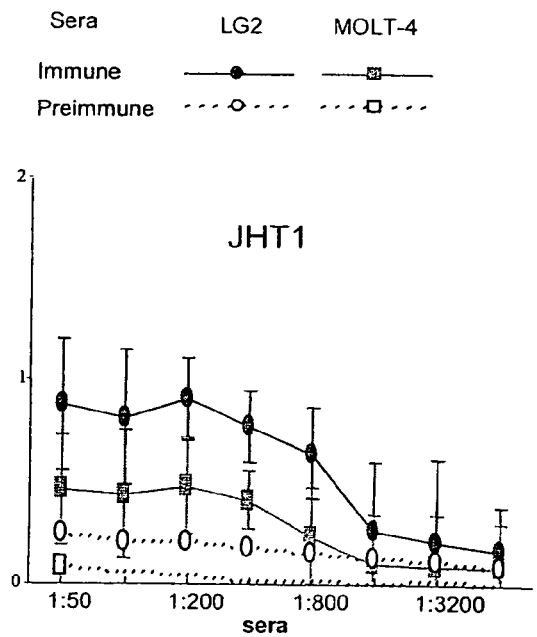
FIG. 2B is a graphical representation of data demonstrating that HLA class II peptide mimic JHT1 elicits a humoral immune response against HLA class II antigens in BALB/c mice.
Figure 4A:
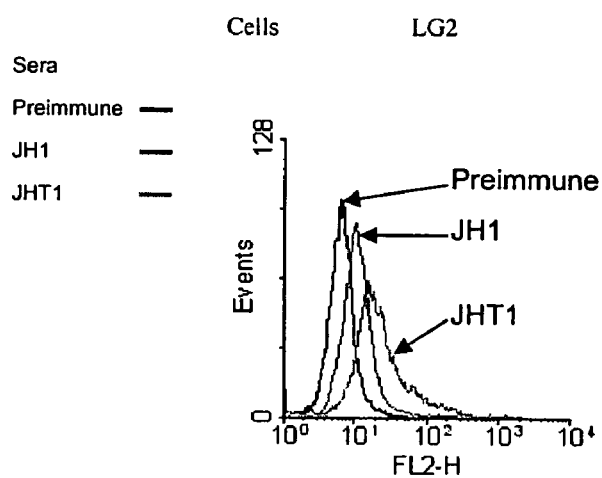
FIG. 4A. is a graphical representation of flow cytometry data demonstrating reactivity of with HLA class II antigens of LG2 lymphoid cells with immune sera from mice immunized with JH1 and JHT1.
Figure 4B:
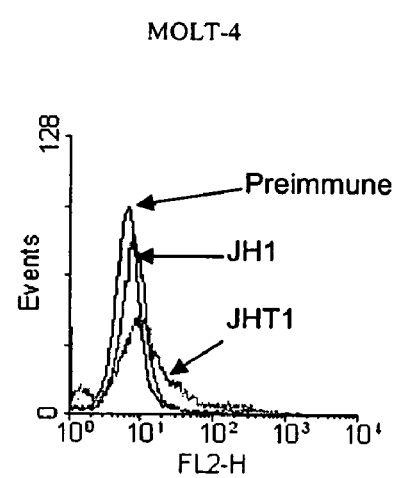
FIG. 4B. is a graphical representation of flow cytometry data demonstrating lack of reactivity with control MOLT-4 lymphoid cells with immune sera from mice immunized with JH1 and JHT1.

HLA-DR transgenic mice express HLA-DR molecules. The promoter that is used to drive DR expression in the transgenic mice is H2 Ea promoter (pDOI-5 expression vector). This vector directs the expression of cDNA to cells which normally display class II molecules. HLA-DR transgenic mice were utilized as a model to test whether HLA class II peptide mimics can break tolerance to self-antigen. HLA-DR transgenic mice were immunized with peptide JH1 and JHT1 conjugated to keyhole limpet hemocyanin (KLH) and mixed with complete Freund's adjuvant for priming and with incomplete Freund's adjuvant for boosting. As shown in FIGS. 2A-2B, 3A-3B and 4A-4B, high-titer antibodies to the immunizing peptides were detected in the sera of immunized mice. In addition, anti-HLA class II antibodies were detected in the sera of immunized mice at lower titers. These experiments utilized LG2 cells as described in Example 2 and MOLT-4 cells. MOLT-4 cells are a human T lymphoblast cell line which does not express HLA class II antigens. It was used as a control. Sera used for testing reactivity with HLA class II antigens was harvested on day 35 from BABL/c mice for FIGS. 2 and 4 and on day 70 from HLA-DR transgenic mice in FIG. 3. For FIGS. 2, 3 and 4, preimmune serum was harvested one week before the first immunization and was used as a control. The results as shown in FIG. 2A demonstrate JH1 induced a humoral response against HLA class II antigens in BALB/c mice. The results as shown in FIG. 2B demonstrate JHT1 also induced a humoral response against HLA class II antigens in BALB/c mice. The results as shown in FIG. 3A demonstrate that JH1 can break self-tolerance in HLA-DR mice which express HLA class II antigens, while the results in FIG. 3B demonstrate that JHT1 can also break self-tolerance in HLA-DR mice. One intradermal injection with HLA class II bearing LG2 cells enhanced the immune response to HLA class II antigens. No obvious side effects have been observed in the immunized mice Thus, the compositions and methods described herein demonstrate that HLA class II peptide mimics can overcome unresponsiveness to self-HLA class II antigens and elicit a humoral immune response to HLA class II.

Having described the preferred embodiments of the present invention, it will be apparent to one of ordinary skill in the art that various modifications may be made to the disclosed embodiments, and that such modifications are intended to be within the scope of the present invention.

REFERENCES

1. American Cancer Society: Cancer Facts & FIGS. 2002. (2002) American Cancer Society, Inc.
2. Lesinski, G. B., Smithson, S. L. Srivastava, N., Chen, D., Widera, G., and Westerink, M. A. (2001). A DNA vaccine encoding a peptide mimic of *Streptoccoccus pneumoniate* serotype 4 capsular polysaccharide induces specific anti-carbohydrate antibodies in Balb/c mice. Vaccine 19, 1717-1726.
3. Luo, P., Canziani, G., Cunto-Amesty, G., and Kieber-Emmons, T. (2000). A molecular basis for functional peptide mimicry of a carbohydrate antigen. J. Bio. Chem. 275, 16146-16154.
4. Chapman, P. B., Livingston, P. O., Morrison, M. E., Williams, L., Houghton, A. N. (1994). Immunization of melanoma patients with anti-idiotypic monoclonal antibody BEC2 (which mimics GD3 ganglioside): Pilot trials using no immunological adjuvant. Vaccine Res. 3, 59-69.
5. McCaffery, M., Yao, T. J., Williams, L., Livingston, P. O., Houghton, A. N., Chapman, P. B. (1996). Immunization of melanoma patients with BEC2 anti-idiotypic monoclonal antibody that mimics GD3 ganglioside; enhanced immunogenicity when combined with adjuvant. Clin. Cancer Res. 2, 679-686.
6. Grant, S. C., Kris, M. G., Houghton, A. N., Chapman, P. B. (1999). Long survival of patients with small cell lung cancer after adjuvant treatment with the anti-idiotypic antibody BEC2 plus bacillus calmette-guerin. Clin. Cancer Res. 5, 1319-1323.
7. Mittelman A, Chen Z J, Yang H, Wong G Y and Ferrone S. (1992) Human high molecular weight melanoma-associated antigen (HMW-MAA) mimicry by mouse anti-idiotypic monoclonal antibody MK2-23: induction of humoral anti-HMW-MAA immunity and prolongation of survival in patients with stage IV melanoma. Proc Natl Acad Sci USA. 89:466-70.

What is claimed is:

1. An isolated and purified peptide which blocks the binding of an anti-HLA class II antibody to a cell expressing HLA class II antigen and is capable of eliciting antibodies reactive against HLA class II antigen, wherein the sequence of the peptide is selected from the group consisting of SEQ ID NO:1, SEQ ID NO:2, SEQ ID NO:3, SEQ ID NO:4, SEQ ID NO:5, SEQ ID NO:7 and SEQ ID NO:8.

2. The peptide of claim 1 wherein the sequence of the peptide is SEQ ID NO:1.

3. The peptide of claim 1 wherein the sequence of the peptide is SEQ ID NO:5.

4. An antigenic composition comprising a pharmaceutically acceptable carrier and a peptide which blocks the binding of an anti-HLA class II antibody to a cell bearing HLA class II antigen and is capable of eliciting antibodies reactive against HLA class II antigen, wherein the peptide consists of a sequence selected from the group consisting of SEQ ID NO:1, SEQ ID NO:2, SEQ ID NO:3, SEQ ID NO:4, SEQ ID NO:5.

5. The antigenic composition of claim 4, wherein the peptide consists of the sequence of SEQ ID NO:1.

6. The antigenic composition of claim 4, wherein the peptide consists of the sequence of SEQ ID NO:5.

* * * * *

SEQUENCE LISTING

```
<160> NUMBER OF SEQ ID NOS: 8

<210> SEQ ID NO 1
<211> LENGTH: 12
<212> TYPE: PRT
<213> ORGANISM: artificial sequence
<220> FEATURE:
<221> NAME/KEY: unknown
<222> LOCATION:
<223> OTHER INFORMATION: synthesized peptide JH1

<400> SEQUENCE: 1

Ser Cys Leu Arg Ala Gly Gly Trp Val Cys Cys Lys
 1               5                  10      12

<210> SEQ ID NO 2
<211> LENGTH: 12
<212> TYPE: PRT
<213> ORGANISM: artificial sequence
<220> FEATURE:
<221> NAME/KEY: unknown
<222> LOCATION:
<223> OTHER INFORMATION: synthesized peptide JH2

<400> SEQUENCE: 2

Tyr Cys Gly Tyr Thr Asn Glu Tyr Lys Cys Cys Tyr
 1               5                  10      12

<210> SEQ ID NO 3
<211> LENGTH: 15
<212> TYPE: PRT
```

```
<213> ORGANISM: artificial sequence
<220> FEATURE:
<221> NAME/KEY: unknown
<222> LOCATION:
<223> OTHER INFORMATION: synthesized peptide JH3

<400> SEQUENCE: 3

Met Thr Thr Arg Val Thr Arg Thr Ala Gly Asn Asn Ala Val Ser
 1               5                  10                  15

<210> SEQ ID NO 4
<211> LENGTH: 15
<212> TYPE: PRT
<213> ORGANISM: artificial sequence
<220> FEATURE:
<221> NAME/KEY: unknown
<222> LOCATION:
<223> OTHER INFORMATION: synthesized peptide JH4

<400> SEQUENCE: 4

Gln Pro Ser Leu Thr Gly Ile Gln Arg Pro Glu Phe Gln Leu Arg
 1               5                  10                  15

<210> SEQ ID NO 5
<211> LENGTH: 12
<212> TYPE: PRT
<213> ORGANISM: artificial sequence
<220> FEATURE:
<221> NAME/KEY: unknown
<222> LOCATION:
<223> OTHER INFORMATION: synthesized peptide JHT1

<400> SEQUENCE: 5

Lys Cys Pro Leu Asp Pro Lys Gly Leu Asn Cys Val
 1               5                  10      12

<210> SEQ ID NO 6
<211> LENGTH: 12
<212> TYPE: PRT
<213> ORGANISM: artificial sequence
<220> FEATURE:
<221> NAME/KEY: unknown
<222> LOCATION:
<223> OTHER INFORMATION: synthesized peptide JH1

<400> SEQUENCE: 6

Ser Cys Leu Arg Ala Gly Gly Trp Val Cys Cys Lys
 1               5                  10      12

<210> SEQ ID NO 7
<211> LENGTH: 12
<212> TYPE: PRT
<213> ORGANISM: artificial sequence
<220> FEATURE:
<221> NAME/KEY: unknown
<222> LOCATION:
<223> OTHER INFORMATION: synthesized peptide JH2

<400> SEQUENCE: 7

Tyr Cys Gly Tyr Thr Asn Glu Tyr Lys Cys Cys Val
 1               5                  10      12

<210> SEQ ID NO 8
<211> LENGTH: 15
<212> TYPE: PRT
<213> ORGANISM: artificial sequence
<220> FEATURE:
<221> NAME/KEY: unknown
<222> LOCATION:
```

-continued

```
<223> OTHER INFORMATION: synthesized peptide JTP1

<400> SEQUENCE: 8

Leu Arg Ala Ser Ile Phe Gly Glu Ile Pro Thr Arg Thr Ser Ser
  1               5                  10                  15
```